(12) United States Patent
Endo et al.

(10) Patent No.: US 7,309,587 B2
(45) Date of Patent: Dec. 18, 2007

(54) PROCESS FOR PRODUCING β 1,3-N-ACETYLGLUCOSAMINYL-TRANSFERASE AND N-ACETYLGLUCOSAMINE-CONTAINING COMPLEX CARBOHYDRATE

(75) Inventors: Tetsuo Endo, Palo Alto, CA (US); Satoshi Koizumi, Yokohama (JP)

(73) Assignee: Kyowa Jakko Kogyo Co., Ltd., Tokyo (JP)

( * ) Notice: Subject to any disclaimer, the term of this patent is extended or adjusted under 35 U.S.C. 154(b) by 369 days.

(21) Appl. No.: 10/493,493

(22) PCT Filed: Oct. 25, 2002

(86) PCT No.: PCT/JP02/11111

§ 371 (c)(1),
(2), (4) Date: Apr. 22, 2004

(87) PCT Pub. No.: WO03/035877

PCT Pub. Date: May 1, 2003

(65) Prior Publication Data

US 2005/0003478 A1 Jan. 6, 2005

(30) Foreign Application Priority Data

Oct. 26, 2001 (JP) .............................. 2001-329288

(51) Int. Cl.
- *C02Q 1/48* (2006.01)
- *G01N 33/53* (2006.01)
- *C12P 21/06* (2006.01)
- *C12P 21/04* (2006.01)
- *C12P 19/18* (2006.01)
- *C12N 9/10* (2006.01)
- *C07H 21/04* (2006.01)

(52) U.S. Cl. .................. 435/84; 435/193; 435/7.2; 435/69.1; 435/72; 435/97; 435/274; 435/15; 536/23.1; 536/23.2

(58) Field of Classification Search .................. 435/89, 435/101, 193, 235.1, 320.1; 536/23.2, 53
See application file for complete search history.

(56) References Cited

U.S. PATENT DOCUMENTS

2002/0142425 A1 10/2002 Miyake et al. .............. 435/193
2002/0150968 A1* 10/2002 Wang et al. .................. 435/53
2004/0115763 A1* 6/2004 Narimatsu et al. ......... 435/69.1

FOREIGN PATENT DOCUMENTS

JP 5-244944 9/1993

OTHER PUBLICATIONS

May et al., Complete genomic sequence of *Pasteurella multocida*, Pm 70. PNAS., 2001, vol. 98, No. 6: 3460-3465.*
Zhou et al., A beta-1,3-N-acetylglucosaminyltransferase with poly-N-acetyllactosamine synthase activity is structurally related to beta-1,3-galactosylltransferases. PNAS., 1999, vol. 96: 406-411.*
Katsutoshi Sasaki et al., "Expression Cloning of cDNA Encoding a Human β-1,3-*N*-Acetylglucosaminyltransferase That is Essential for Poly-*N*-Acetyllactosamine Synthesis", *Proc. Natl. Acad. Sci. USA*, vol. 94, Dec. 1997, pp. 14294-14299.
Dapeng Zhou et al., "A β-1,3-*N*-Acetylglucosaminyltransferase With Poly-*N*-Acetyllactosamine Synthase Activity is Structurally Related to β-1,3-Galactosyltransferases", *Proc. Natl. Acad. Sci USA*, vol. 96, Jan. 1999, pp. 406-411.
Ola Blixt et al., "High-level Expression of the *Neisseria meningitidis IgtA* Gene in *Escherichia coli* and Characterization of the Encoded *N*-Acetylglucosaminyltransferase as a Useful Catalyst in the Synthesis of GlcNAcβ1→3Gal and GalNAcβ1→3Gal Linkages", *Glycobiology*, vol. 9, No. 10, 1999, pp. 1061-1071.
Fengyang Yan et al., "Polymer-Supported and Chemoenzymatic Synthesis of the *Neisseria meningitidis* Pentasaccharide: A Methodological Comparison", *Carbohydrate Research*, vol. 328, 2000, pp. 3-16.
Sean Egan et al., "Molecular Cloning and Expression Analysis of a Mouse UDP-GlcNAc:Gal(β1-4)Glc(NAc)-R β1,3-*N*-Acetylglucosaminyltransferase Homologous to *Drosophila melanogaster* Brainiac and the β1,3-Galactosyltransferase Family", *Glycoconjugate Journal*, vol. 17, 2000, pp. 867-875.
Barbara J. May et al., "Complete Genomic Sequence of *Pasteurella multocida*, Pm70", *PNAS*, vol. 98, No. 6, Mar. 13, 2001, pp. 3460-3465.
Murata, et al., "Facile enzymatic conversion of lactose into lacto-N-tetraose and lacto-N-neotetraose", *Glycoconjugate Journal*, vol. 16, No. 3 (1999), pp. 189-195.

* cited by examiner

*Primary Examiner*—Rebecca E. Prouty
*Assistant Examiner*—Ganapathirama Raghu
(74) *Attorney, Agent, or Firm*—Fitzpatrick, Cella, Harper & Scinto (57) ABSTRACT

The present invention can provide a process for producing a protein having β1,3-N-acetylglucosaminyltransferase activity using a transformant comprising a DNA encoding a protein having β1,3-N-acetylglucosaminyltransferase activity derived from a microorganism belonging to the genus *Pasteurella* and a process for producing an N-acetylglucosamine-containing complex carbohydrate using a transformant capable of producing a protein having β1,3-N-acetylglucosaminyltransferase activity derived from a microorganism.

8 Claims, 1 Drawing Sheet

SEQUENCE LISTING

<160> NUMBER OF SEQ ID NOS: 4

<210> SEQ ID NO 1
<211> LENGTH: 294
<212> TYPE: PRT
<213> ORGANISM: Pasteurella multocida

<400> SEQUENCE: 1

Met Phe Ser Ile Ile Val Pro Ser Tyr Asn Arg Gln Ala Glu Ile Pro
 1               5                  10                  15

Ala Leu Leu Glu Ser Leu His Gln Gln Thr Val Thr His Phe Glu Val
            20                  25                  30

Ile Ile Val Asp Asp Cys Ser Arg Glu Pro Val Glu Ile Asn Gln Lys
        35                  40                  45

Tyr Ala Phe Pro Cys Thr Val Ile Arg Asn Pro Gln Asn Leu Gly Ala
    50                  55                  60

Ala Glu Ser Arg Asn Val Gly Ala Arg Gln Ala His Tyr Asp Trp Leu
65                  70                  75                  80

Leu Phe Leu Asp Asp Asp Asp Arg Phe Val Asn Glu Lys Cys Ala Val
                85                  90                  95

Leu Ala Glu Ala Ile Thr Gln His Pro Glu Val Asn Phe Ile Tyr His
            100                 105                 110

Pro Ala His Cys Val Met Val Asn Glu Gly Phe Thr Tyr Gln Thr His
        115                 120                 125

Pro Tyr Ala Asp Pro Ala Leu Leu Thr Leu Glu Asn Leu Leu Arg Ala
    130                 135                 140

Asn Lys Ile Gly Gly Met Pro Met Ile Ala Val Gln Lys Ser Leu Phe
145                 150                 155                 160

Leu Lys Val Gly Gly Leu Ser Ser Tyr Leu Arg Ala Leu Glu Asp Tyr
                165                 170                 175

Glu Phe Leu Leu Lys Leu Val Ser Asp Glu Asp Phe Gln Pro Leu Tyr
            180                 185                 190

```
Val Glu Gln Ala Leu Thr Arg Cys Thr Phe His Thr Lys Arg Ala Ser
            195                 200                 205

Val Ser Thr Asn Thr Ser His Thr Glu Gln Ala Ile Glu Glu Ile Lys
            210                 215                 220

Ala Arg Tyr Val Lys Thr Thr Gln Gln Ala Gln Ala Phe Glu Leu Asn
225                 230                 235                 240

Ala Leu Tyr Met Leu Ala Tyr Pro His Met Met Asn Leu Ser Arg Gly
            245                 250                 255

Ala Ala Arg Tyr Tyr Ala Ser Met Phe Arg Lys Ser Gly Gln Ile Lys
            260                 265                 270

Tyr Gly Ile Leu Ala Leu Leu Thr Cys Leu Ser Pro Lys Leu Val Ile
            275                 280                 285

Gln Met Lys Arg Val Ile

<210> SEQ ID NO 2
<211> LENGTH: 882
<212> TYPE: DNA
<213> ORGANISM: Pasteurella multocida

<400> SEQUENCE: 2 atg ttt agt att att gtg ccg tct tac aat cga caa gcg gaa atc cct       48
Met Phe Ser Ile Ile Val Pro Ser Tyr Asn Arg Gln Ala Glu Ile Pro
  1               5                  10                  15 gcg ttg ttg gaa agt tta cat cag caa acc gta acg cat ttt gaa gtt       96
Ala Leu Leu Glu Ser Leu His Gln Gln Thr Val Thr His Phe Glu Val
             20                  25                  30 att att gtc gat gat tgt tcc cgt gaa ccg gtt gag atc aat caa aaa   144
Ile Ile Val Asp Asp Cys Ser Arg Glu Pro Val Glu Ile Asn Gln Lys
         35                  40                  45 tat gct ttt cct tgc aca gtc atc cgc aat ccg caa aat tta ggg gcg   192
Tyr Ala Phe Pro Cys Thr Val Ile Arg Asn Pro Gln Asn Leu Gly Ala
     50                  55                  60 gca gaa agt cgt aat gtg ggg gca aga caa gcg cat tat gac tgg tta   240
Ala Glu Ser Arg Asn Val Gly Ala Arg Gln Ala His Tyr Asp Trp Leu
 65                  70                  75                  80 ctt ttt tta gat gat gat gat cgt ttt gta aac gaa aaa tgt gcg gtt   288
Leu Phe Leu Asp Asp Asp Asp Arg Phe Val Asn Glu Lys Cys Ala Val
                 85                  90                  95 tta gcc gag gct atc aca caa cat ccg gaa gtg aac ttt att tat cat   336
Leu Ala Glu Ala Ile Thr Gln His Pro Glu Val Asn Phe Ile Tyr His
            100                 105                 110 cct gcc cat tgt gtg atg gtt aat gaa ggg ttt act tac cag acc cac   384
Pro Ala His Cys Val Met Val Asn Glu Gly Phe Thr Tyr Gln Thr His
        115                 120                 125 cct tat gca gac cct gcg tta tta acc tta gag aat ctg ctc cgt gcc   432
Pro Tyr Ala Asp Pro Ala Leu Leu Thr Leu Glu Asn Leu Leu Arg Ala
    130                 135                 140 aat aaa att ggt ggg atg ccg atg att gcg gtg caa aaa tcg ctt ttt   480
Asn Lys Ile Gly Gly Met Pro Met Ile Ala Val Gln Lys Ser Leu Phe
145                 150                 155                 160 tta aaa gtt ggc ggg tta tct tct tat tta agg gca ttg gaa gac tat   528
Leu Lys Val Gly Gly Leu Ser Ser Tyr Leu Arg Ala Leu Glu Asp Tyr
                165                 170                 175 gag ttt ttg tta aag ctg gtg tct gat gaa gat ttc caa cct tta tat   576
Glu Phe Leu Leu Lys Leu Val Ser Asp Glu Asp Phe Gln Pro Leu Tyr
            180                 185                 190 gtg gag caa gca ttg aca cgt tgt act ttt cat acc aaa cgt gcc agt   624
Val Glu Gln Ala Leu Thr Arg Cys Thr Phe His Thr Lys Arg Ala Ser
        195                 200                 205
```

-continued

```
gta tcc acc aat act tca cat acg gaa cag gcg att gaa gaa att aaa    672
Val Ser Thr Asn Thr Ser His Thr Glu Gln Ala Ile Glu Glu Ile Lys
    210             215                 220 gca cgt tat gtt aaa acg aca caa caa gca caa gcg ttt gag tta aat    720
Ala Arg Tyr Val Lys Thr Thr Gln Gln Ala Gln Ala Phe Glu Leu Asn
225                 230                 235                 240 gcg tta tat atg ctg gcg tat ccc cat atg atg aat tta tca cgg ggc    768
Ala Leu Tyr Met Leu Ala Tyr Pro His Met Met Asn Leu Ser Arg Gly
                245                 250                 255 gct gca cgt tat tac gcc agc atg ttt cgc aaa agc ggg caa atc aaa    816
Ala Ala Arg Tyr Tyr Ala Ser Met Phe Arg Lys Ser Gly Gln Ile Lys
            260                 265                 270 tat ggt ata ttg gcg tta ctt acc tgt ctt tcg cct aaa ttg gtt att    864
Tyr Gly Ile Leu Ala Leu Leu Thr Cys Leu Ser Pro Lys Leu Val Ile
        275                 280                 285 cag atg aaa agg gtt att                                            882
Gln Met Lys Arg Val Ile
```

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence:Synthetic DNA

<400> SEQUENCE: 3
gaggaagctt aatgtttagt attatt                                       26

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence:Synthetic DNA

<400> SEQUENCE: 4
ctgaggatcc cattaaataa ccctttcat                                    30

PROCESS FOR PRODUCING β 1,3-N-ACETYLGLUCOSAMINYL-TRANSFERASE AND N-ACETYLGLUCOSAMINE-CONTAINING COMPLEX CARBOHYDRATE

TECHNICAL FIELD

The present invention relates to a process for producing a protein having β1,3-N-acetylglucosaminyltransferase activity using a transformant comprising a DNA encoding a protein having β1,3-N-acetylglucosaminyltransferase activity and a process for producing an N-acetylglucosamine-containing complex carbohydrate using the transformant.

BACKGROUND ART

As β1,3-N-acetylglucosaminyltransferase and its genes, genes derived from animals [*Proc. Natl. Acad. Sci. U.S.A.*, 96, 406 (1999), *J. Biol. Chem.*, 276, 3498 (2001)] and the like have been obtained. However, there is no example in which the β1,3-N-acetylglucosaminyltransferase derived from an animal was expressed in a microorganism, such as *Escherichia coli*, as a protein having activity.

On the other hand, in the case of microorganisms, there is a report in which a gene encoding the β1,3-N-acetylglucosaminyltransferase was obtained from a microorganism belonging to the genus *Neisseria* and the β1,3-N-acetylglucosaminyltransferase was expressed in *Escherichia coli* using the gene [*Carbohydr. Res.*, 328, 3 (2000); *Glycobiology*, 9, 1061 (1999)]. However, there is no report in which the gene is obtained from a microorganism belonging to the genus *Pasteurella*.

Also, all nucleotide sequences of the genomic DNA in *Pasteurella multocida* PM70 have been determined [*Proc. Natl. Acad. Sci. USA*, 98, 3460 (2001)], and it has been suggested that pm0511 gene is a gene encoding glycosyltransferase by homology search and the like (http://www.cbc.umn.edu/ResearchProjects/Pm/pmhome.html). However, there is no report that the gene product has β1,3-N-acetylglucosaminyltransferase activity.

DISCLOSURE OF THE INVENTION

Objects of the present invention are to provide a process for producing a protein having β1,3-N-acetylglucosaminyltransferase activity using a transformant comprising a DNA encoding a protein having β1,3-N-acetylglucosaminyltransferase activity and a process for producing an N-acetylglucosamine-containing complex carbohydrate using the transformant.

Specifically, the present invention relates to the following (1) to (28):

(1) A process for producing a protein having β1,3-N-acetylglucosaminyltransferase activity, which comprises: culturing a transformant capable of producing the protein derived from a microorganism belonging to the genus *Pasteurella* in a medium to produce and accumulate the protein in the culture, and recovering the protein from the culture.

(2) The process according to (1), wherein the microorganism belonging to the genus *Pasteurella* is *Pasteurella multocida*.

(3) The process according to (1), wherein the protein having β1,3-N-acetylglucosaminyltransferase activity is a protein comprising the amino acid sequence represented by SEQ ID NO:1.

(4) The process according to (1), wherein the protein having β1,3-N-acetylglucosaminyltransferase activity is a protein which consists of an amino acid sequence in which at least one amino acid is deleted, substituted or added in the amino acid sequence represented by SEQ ID NO:1, and has β1,3-N-acetylglucosaminyltransferase activity.

(5) The process according to (1), wherein the protein having β1,3-N-acetylglucosaminyltransferase activity is a protein which has a homology of at least 80% with the amino acid sequence represented by SEQ ID NO:1, and has β1,3-N-acetylglucosaminyltransferase activity.

(6) The process according to (1), wherein the transformant is a transformant which comprises a recombinant DNA comprising a DNA encoding a protein having β1,3-N-acetylglucosaminyltransferase activity.

(7) The process according to (6), wherein the transformant is obtained by using a microorganism as a host cell.

(8) The process according to (7), wherein the microorganism is *Escherichia coli*.

(9) The process according to (6), wherein the DNA encoding the protein having β1,3-N-acetylglucosaminyltransferase activity is a DNA comprising the nucleotide sequence represented by SEQ ID NO:2.

(10) The process according to (6), wherein the DNA encoding the protein having β1,3-N-acetylglucosaminyltransferase activity is a DNA which hybridizes with a DNA comprising the nucleotide sequence represented by SEQ ID NO:2 under stringent conditions, and encodes a protein having β1,3-N-acetylglucosaminyltransferase activity.

(11) A process for producing an N-acetylglucosamine-containing complex carbohydrate, which comprises: allowing a culture of a transformant capable of producing a protein having β1,3-N-acetylglucosaminyltransferase activity or a treated product of the culture as an enzyme source, uridine 5'-diphosphate N-acetylglucosamine and an acceptor complex carbohydrate to be present in an aqueous medium to produce and accumulate the N-acetylglucosamine-containing complex carbohydrate in the aqueous medium, and recovering the N-acetylglucosamine-containing complex carbohydrate from the aqueous medium.

(12) The process according to (11), wherein the treated product of the culture is selected from the group consisting of a concentrated product of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells and an enzyme preparation obtained by extracting from the cells.

(13) The process according to (11), wherein the acceptor complex carbohydrate is a complex carbohydrate comprising an oligosaccharide having galactose in its non-reducing terminal.

(14) The process according to (13), wherein the oligosaccharide having galactose in the non-reducing terminal is an oligosaccharide selected from the group consisting of lactose, N-acetyllactosamine, lacto-N-tetraose and lacto-N-neotetraose.

(15) The process according to (11), wherein the acceptor complex carbohydrate is a complex carbohydrate selected from the group consisting of lactose, N-acetyllactosamine, lacto-N-tetraose, and lacto-N-neotetraose.

(16) The process according to (11), wherein the protein having β1,3-N-acetylglucosaminyltransferase is a protein derived from a microorganism belonging to the genus *Pasteurella*.

(17) The process according to (16), wherein the microorganism belonging to the genus *Pasteurella* is *Pasteurella multocida*.

(18) The process according to (11), wherein the protein having β1,3-N-acetylglucosaminyltransferase activity is a protein comprising the amino acid sequence represented by SEQ ID NO:1.

(19) The process according to (11), wherein the protein having β1,3-N-acetylglucosaminyltransferase activity is a protein which consists of an amino acid sequence in which at least one amino acid is deleted, substituted or added in the amino acid sequence represented by SEQ ID NO:1, and has β1,3-N-acetylglucosaminyltransferase activity.

(20) The process according to (11), wherein the protein having β1,3-N-acetylglucosaminyltransferase activity is a protein which has a homology of at least 80% with the amino acid sequence represented by SEQ ID NO:1, and has β1,3-N-acetylglucosaminyltransferase activity.

(21) The process according to (11), wherein the transformant is a transformant which comprises a recombinant DNA comprising a DNA encoding a protein having β1,3-N-acetylglucosaminyltransferase activity.

(22) The process according to (21), wherein the transformant is obtained by using a microorganism as a host cell.

(23) The process according to (22), wherein the microorganism is *Escherichia coli*.

(24) The process according to (21), wherein the DNA encoding the protein having β1,3-N-acetylglucosaminyltransferase activity is a DNA comprising the nucleotide sequence represented by SEQ ID NO:2.

(25) The process according to (21), wherein the DNA encoding the protein having β1,3-N-acetylglucosaminyltransferase activity is a DNA which hybridizes with a DNA comprising the nucleotide sequence represented by SEQ ID NO:2 under stringent conditions, and encodes a protein having β1,3-N-acetylglucosaminyltransferase activity.

(26) A protein having β1,3-N-acetylglucosaminyltransferase activity, which comprises the amino acid sequence represented by SEQ ID NO:1.

(27) A protein which consists of an amino acid sequence in which at least one amino acid is deleted, substituted or added in the amino acid sequence represented by SEQ ID NO:1, and has β1,3-N-acetylglucosaminyltransferase activity.

(28) A DNA which hybridizes a DNA comprising the nucleotide sequence represented by SEQ ID NO:2 under stringent conditions, and encodes a protein having β1,3-N-acetylglucosaminyltransferase activity.

The present invention is explained below in detail.

The protein having β1,3-N-acetylglucosaminyltransferase activity of the present invention includes a protein comprising the amino acid sequence represented by SEQ ID NO:1; and a protein which consists of an amino acid sequence in which at least one amino acid is deleted, substituted or added in the amino acid sequence represented by SEQ ID NO:1.

The protein having β1,3-N-acetylglucosaminyltransferase activity used in the process for production of a complex carbohydrate of the present invention is not particularly limited, so long as the protein is derived from a microorganism. It is preferably the protein derived from a microorganism belonging to the genus *Pasteurella*, and more preferably the protein derived from *Pasteurella multocida*. Specifically, the protein includes a protein comprising the amino acid sequence represented by SEQ ID NO:1; a protein which consists of an amino acid sequence in which at least one amino acid is deleted, substituted or added in the amino acid sequence represented by SEQ ID NO:1, and has β1,3-N-acetylglucosaminyltransferase activity; and a protein which has a homology of at least 80% with the amino acid sequence represented by SEQ ID NO:1, and has β1,3-N-acetylglucosaminyltransferase activity.

The protein which consists of an amino acid sequence in which at least one amino acid is deleted, substituted or added, and has β1,3-N-acetylglucosaminyltransferase activity can be obtained, for example, by introducing mutation(s) to a DNA encoding a protein comprising the amino acid sequence represented by SEQ ID NO:1 according to a method for introducing site-directed mutagenesis described in *Molecular Cloning, A Laboratory Manual*, Second Edition, Cold Spring Harbor Laboratory Press (1989) (hereinafter referred to as "*Molecular Cloning*, Second Edition"); *Current Protocols in Molecular Biology*, John Wiley & Sons (1987-1997) (hereinafter referred to as "*Current Protocols in Molecular Biology*"); *Nucleic Acids. Research*, 10, 6487 (1982); *Proc. Natl. Acad. Sci. USA*, 79, 6409 (1982); *Gene*, 34, 315 (1985); *Nucleic Acids. Research*, 13, 4431 (1985); *Proc. Natl. Acad. Sci. USA*, 82, 488 (1985) and the like.

The number of the amino acids which are deleted, substituted or added is not particularly limited; however, it is such a number that deletion, substitution or addition can be carried out by a known method such as method for introducing site-directed mutagenesis. The number is 1 to several tens, preferably 1 to 20, more preferably 1 to 10, and most preferably 1 to 5.

The deletion, substitution or addition of at least one amino acid residue in the amino acid sequence represented by SEQ ID NO:1 means that one or at least two amino acids are deleted, substituted or added at any position in the same sequence. The deletion, substitution or addition can be carried out in the same amino acid sequence simultaneously. Also, the amino acid residue substituted or added can be natural or non-natural. The natural amino acid residue includes L-alanine, L-asparagine, L-aspartic acid, L-glutamine, L-glutamic acid, glycine, L-histidine, L-isoleucine, L-leucine, L-lysine, L-arginine, L-methionine, L-phenylalanine, L-proline, L-serine, L-threonine, L-tryptophan, L-tyrosine, L-valine, L-cysteine, and the like.

Herein, examples of amino acid residues which are substituted with each other are shown below. Amino acid residues in the same group can readily be substituted with each other.

Group A:
  leucine, isoleucine, norleucine, valine, norvaline, alanine, 2-aminobutanoic acid, methionine, O-methylserine, t-butylglycine, t-butylalanine, cyclohexylalanine;

Group B:
  aspartic acid, glutamic acid, isoasparatic acid, isoglutamic acid, 2-aminoadipic acid, 2-aminosuberic acid;

Group C:
  asparagine, glutamine;

Group D:
  lysine, arginine, ornithine, 2,4-diaminobutanoic acid, 2,3-diaminopropionic acid;

Group E:
  proline, 3-hydroxyproline, 4-hydroxyproline;

Group F:
    serine, threonine, homoserine;

Group G:
    phenylalanine, tyrosine.

Also, in order that the protein which consists of an amino acid sequence in which at least one amino acid is deleted, substituted or added has β1,3-N-acetylglucosaminyltransferase activity, the protein has a homology of preferably at least 80% or more, more preferably 90% or more, and most preferably 95% or more, with the amino acid sequence represented by SEQ ID NO:1.

The homology of an amino acid sequence or a nucleotide sequence can be determined by using the algorithm BLAST by Karlin and Altschl [*Proc. Natl. A cad. Sci. USA*, 90,5873 (1993)] or FASTA [*Methods Enzymol.*, 183, 63 (1990)]. The programs called BLASTN and BLASTX have developed based on the above algorithm BLAST [*J. Mol. Biol.*, 215, 403 (1990)]. In the case of analyzing a nucleotide sequence by BLASTN based on BLAST, for example, the parameter can be set to score=100, wordlength=12. Also, in the case of analyzing an amino acid sequence by BLASTX based on BLAST, for example, the parameter can be set to score=50, wordlength=3. When BLAST and Gapped BLAST programs are used, a default parameter of each program can be used. The specific analysis methods of using the above programs are known (http://www.ncbi.nlm.nih.gov.).

The transformant used in the production of the protein having β1,3-N-acetylglucosaminyltransferase activity of the present invention includes a transformant comprising a DNA encoding a protein having β1,3-N-acetylglucosaminyltransferase. The DNA encoding the protein having β1,3-N-acetylglucosaminyltransferase includes (1) a DNA encoding a protein comprising the amino acid sequence represented by SEQ ID NO:1;
(2) a DNA comprising the nucleotide sequence represented by SEQ ID NO:2;
(3) a DNA encoding a protein which consists of an amino acid sequence in which at least one amino acid is deleted, substituted or added in the amino acid sequence represented by SEQ ID NO:1, and has β1,3-N-acetylglucosaminyltransferase activity;
(4) a DNA encoding a protein which has a homology of at least 80% with the amino acid sequence represented by SEQ ID NO:1, and has β1,3-N-acetylglucosaminyltransferase activity; and
(5) a DNA which hybridizes with a DNA comprising the nucleotide sequence represented by SEQ ID NO:2 under stringent conditions, and encodes a protein having β1,3-N-acetylglucosaminyltransferase activity.

The DNA which is hybridizable under stringent conditions is a DNA obtained by colony hybridization, plaque hybridization, Southern hybridization or the like using, as a probe, a part or a full length of a DNA consisting of the nucleotide sequence represented by SEQ ID NO:2. Specifically, the DNA includes a DNA which can be identified by carrying out hybridization at 65° C. in the presence of 0.7-1.0 mol/l NaCl using a filter on which a DNA prepared from colonies or plaques is immobilized, and then washing the filter with 0.1× to 2×SSC solution (the composition of 1×SSC solution contains 150 mmol/l sodium chloride and 15 mmol/l sodium citrate) at 65° C. The hybridization can be carried out in accordance with a known method described in, for example, *Molecular Cloning*, Second Edition; *Current Protocols in Molecular Biology; DNA Cloning 1: Core Techniques, A Practical Approach*, Second Edition, Oxford University (1995) or the like. Specifically, the DNA which is hybridizable includes a DNA having a homology of at least 60% or more, preferably 80% or more, and more preferably 95% or more, with the nucleotide sequence represented by SEQ ID NO:2 when calculated based on the above parameters using above BLAST, FASTA or the like.

[1] Preparation of a DNA Used in the Process for Production of the Present Invention (1) Selection of a DNA Encoding the Protein Having β1,3-N-acetylglucosaminyltransferase Activity Using Database The full nucleotide sequence of the genomic DNA in *Pasteurella multocida* PM70 was determined [*Proc. Natl. Acad. Sci., USA*, 98, 3460 (2001)], and the DNA encoding the protein having β1,3-N-acetylglucosaminyltransferase activity can be selected by carrying out gene search, homology search and the like by using, as a query, a known β1,3-N-acetylglucosaminyltransferase gene based on the nucleotide sequence database of the genomic DNA [http://www.cbc.umn.edu/ResearchProjects/Pm/pmhome.html, http://www.ncbi.nlm.nih.gov/BLAST/].

(2) Preparation of a DNA Used in the Process for Production of the Present Invention The DNA encoding the protein having β1,3-N-acetylglucosaminyltransferase activity used in the process for production of the present invention can be prepared from a microorganism belonging to the genus *Pasteurella*. The microorganism belonging to the genus *Pasteurella* includes *Pasteurella multocida*, and specifically *Pasteurella multocida* PM70 (available from Minnesota University) and the like.

The microorganism belonging to *Pasteurella multocida* can be cultured by a known method [for example, *FEMS Microbiol. Lett.,* 166, 289 (1998)].

After the culturing, a chromosomal DNA of the microorganism can be isolated and purified by a known method (for example, method described in *Current Protocols in Molecular Biology*).

A DNA fragment containing the DNA used in the process for production of the present invention can be obtained by preparing a primer based on the nucleotide sequence of the genomic DNA selected in the item (1) and then carrying out PCR [*PCR Protocols*, Academic Press (1990)] using the genomic DNA as a template.

Furthermore, the DNA of interest can be obtained according to a hybridization method by using the synthetic DNA designed based on the nucleotide sequence of the genomic DNA as a probe.

The nucleotide sequence of the DNA can be determined by inserting the obtained DNA as it is or after digestion with an appropriate restriction enzyme, into a vector according to the usual method, and carrying out analysis by the generally used nucleotide sequence analysis method such as the dideoxy method [*Proc. Natl. Acad. Sci. USA,* 74, 5463 (1977)] or a method comprising the use of an apparatus for nucleotide sequence analysis such as 373A-DNA Sequencer (manufactured by Perkin-Elmer).

Based on the nucleotide sequence thus determined, the DNA of interest can also be prepared by chemical synthesis using, for example, DNA Synthesizer 8905 manufactured by Perceptive Biosystems or the like.

The vector into which the DNA of the present invention is inserted includes pBluescript KS(+) (manufactured by Stratagene), pDIRECT [*Nucleic Acids Res.,* 18, 6069 (1990)], pCR-Script Amp SK(+) (manufactured by Stratagene), pT7Blue manufactured by Novagen), pCR II (manufactured by Invitrogen), pCR-TRAP (manufactured by Genehunter) and the like.

pPM0511SK which is a recombinant DNA which comprises the DNA comprising the nucleotide sequence represented by SEQ ID NO:2 has been deposited on Oct. 18, 2001, as FERM BP-7778, in International Patent Organism Depositary, National Institute of Advanced Industrial Science and Technology (Central 6, 1-1, Higashi 1-Chome Tsukuba, Ibaraki, 305-8566, Japan).

The microorganism containing the recombinant DNA which comprises the DNA comprising the sequence represented by SEQ ID NO:2 includes *Escherichia coli* and the like.

*Escherichia coli* includes *Escherichia coli* XL1-Blue, *Escherichia coli* XL2-Blue, *Escherichia coli* DH1, *Escherichia coli* MC1000, *Escherichia coli* KY3276, *Escherichia coli* W1485, *Escherichia coli* JM109, *Escherichia coli* HB101, *Escherichia coli* No.49, *Escherichia coli* W3110, *Escherichia coli* NY49, *Escherichia coli* MP347, *Escherichia coli* NM522, *Escherichia coli* ME8415 and the like.

Any method can be used in the introduction method of the recombinant DNA, so long as it is a method for introducing DNA into the host cell. Examples include the method using a calcium ion [*Proc. Natl. Acad. Sci. USA*, 69, 2110 (1972)], the protoplast method (Japanese Published Unexamined Patent Application No. 248394/88), electroporation [*Nucleic Acid Res.*, 16, 6127 (1988)] and the like.

*Escherichia coli* containing the recombinant DNA which comprises the DNA comprising the nucleotide sequence represented by SEQ ID NO:2 includes *Escherichia coli* NM522/pGT124.

[2] Preparation of the Protein of the Present Invention

The protein having β1,3-N-acetylglucosaminyltransferase activity can be produced by expressing the DNA obtained by the method of the above item [1] in a host cell, for example, as shown below, by using a method described in *Molecular Cloning*, Second Edition, *Current Protocols in Molecular Biology* or the like.

Based on the above DNA, a DNA fragment of an appropriate length containing a portion which encodes the protein can be prepared, if necessary. In addition, productivity of the protein can be improved by substituting a nucleotide in the nucleotide sequence of the protein-coding region so that it has the most suitable codons for the expression in the host.

A recombinant DNA is prepared by inserting the DNA into a downstream of the promoter of an appropriate expression vector.

A transformant capable of producing the protein used for the process of the present invention can be obtained by introducing the recombinant DNA into a host cell suitable for the expression vector.

Any bacteria, yeast strains, animal cells, insect cells, plant cells and the like can be used as the host cell, so long as it can express the gene of interest.

The expression vectors include those which can replicate autonomously in the above host cell or those which can be integrated into a chromosome and have a promoter at such a position that the DNA used in the process for production of the present invention can be transcribed.

When a procaryote such as bacterium is used as the host cell, it is preferred that the recombinant DNA which comprises the DNA encoding the protein of the present invention can replicate autonomously in the procaryote, and that the recombinant vector contains a promoter, a ribosome binding sequence, the DNA of the present invention and a transcription termination sequence. The vector may further comprise a gene regulating the promoter.

The expression vector includes pHelix1 (manufactured by Roche Diagnostics), pKK233-2 (manufactured by Amersham Pharmacia Biotech), pSE280 (manufactured by Invitrogen), pGEMEX-1 (manufactured by Promega), pQE-8 (manufactured by QIAGEN), pET-3 (manufactured by Novagen), pKYP10 (Japanese Published Unexamined Patent Application No. 110600/83), pKYP200 [*Agric. Biol. Chem.*, 48, 669 (1984)], pLSA1 [*Agric. Biol. Chem.*, 53, 277 (1989)], pGEL1 [*Proc. Natl. Acad. Sci. USA*, 82, 4306 (1985)], pBluescript II SK(+), pBluescript II KS(−) (manufactured by Stratagene), pTrs30 [prepared from *Escherichia coli* JM109/pTrS30 (FERM BP-5407)], pTrs32 [prepared from *Escherichia coli* JM109/pTrS32 (FERM BP-5408)], pPAC31 (WO98/12343), pUC19 [*Gene*, 33, 103 (1985)], pSTV28 (manufactured by Takara Shuzo), pUC118 (manufactured by Takara Shuzo), pPA1 (Japanese Published Unexamined Patent Application No. 233798/88) and the like.

Any promoter can be used, so long as it can function in the host cell. Examples include promoters derived from *Escherichia coli*, phage and the like, such as trp promoter ($P_{trp}$), lac promoter ($P_{lac}$), $P_L$ promoter, $P_R$ promoter and $P_{SE}$ promoter, SPO1 promoter, SPO2 promoter, penP promoter and the like. Also, artificially designed and modified promoters, such as a promoter in which two $P_{trp}$ are linked in tandem, tac promoter, lacT7 promoter and letI promoter, can be used.

It is preferred to use a plasmid in which the space between Shine-Dalgarno sequence, which is the ribosome binding sequence, and the initiation codon is adjusted to an appropriate distance (for example, 6 to 18 nucleotides).

The transcription termination sequence to express the DNA used in the process for production of the present invention is not essential for the recombinant DNA. However, it is preferred to lie a transcription terminating sequence immediately downstream of the structural gene.

The procaryotes include a microorganism belonging to the genus *Escherichia*, *Serratia*, *Bacillus*, *Brevibacterium*, *Corynebacterium*, *Microbacterium*, *Pseudomonas* or the like. Examples include *Escherichia coli* XL1-Blue, *Escherichia coli* XL2-Blue, *Escherichia coli* DH1, *Escherichia coli* NM522, *Escherichia coli* MC1000, *Escherichia coli* KY3276, *Escherichia coli* W1485, *Escherichia coli* JM109, *Escherichia coli* HB101, *Escherichia coli* No. 49, *Escherichia coli* W3110, *Escherichia coli* NY49, *Serratia ficaria*, *Serratia fonticola*, *Serratia liquefaciens*, *Serratia marcescens*, *Bacillus subtilis*, *Bacillus amyloliquefaciens*, *Brevibacterium immariophilum* ATCC 14068, *Brevibacterium saccharolyticum* ATCC 14066, *Corynebacterium ammoniagenes*, *Corynebacterium glutamicum* ATCC 13032, *Corynebacterium glutamicum* ATCC 14067, *Corynebacterium glutamicum* ATCC 13869, *Corynebacterium acetoacidophilum* ATCC 13870, *Microbacterium ammoniaphilum* ATCC 15354, *Pseudomonas* sp. D-0110 and the like.

Introduction of the recombinant DNA can be carried out by any methods for introducing DNA into the above-described host cells, such as the method using a calcium ion [*Proc. Natl. Acad. Sci. USA*, 69, 2110 (1972)], the protoplast method (Japanese Published Unexamined Patent Application No. 248394/88) and electroporation [*Nucleic Acids Res*, 16, 6127 (1988)].

When a yeast cell is used as the host cell, the expression vector includes YEp13 (ATCC 37115), YEp24 (ATCC 37051), YCp50 (ATCC 37419), pHS19, pHS15 and the like.

Any promoter can be used so long as it can function in yeast cells. Examples include PHO5 promoter, PGK promoter, GAP promoter, ADH promoter, gal 1 promoter, gal 10 promoter, a heat shock polypeptide promoter, MFα1 promoter, CUP 1 promoter and the like.

The host cell includes a yeast strain belonging to the genus Saccharomyces, Schizosaccharomyces, Kluyveromyces, Trichosporon, Schwanniomyces, Pichia, Candida and the like. Examples include Saccharomyces cerevisiae, Schizosaccharomyces pombe, Kluyveromyces lactis, Trichosporon pullulans, Schwanniomyces alluvius, Pichia pastoris, Candida utilis or the like.

Introduction of the recombinant DNA can be carried out by any of the methods for introducing DNA into a yeast strain, such as electroporation [Methods. Enzymol., 194, 182 (1990)], the spheroplast method [Proc. Natl. Acad. Sci. USA, 81, 4889 (1984)] and the lithium acetate method [J. Bacteriol., 153, 163 (1983)].

When an animal cell is used as the host, the expression vector includes pcDNA1.1, pcDNA1.1/Amp, pCDM8, pREP4 (all manufactured by Invitrogen), pAGE107 (Japanese Published Unexamined Patent Application No. 22979/91), pAS3-3 (Japanese Published Unexamined Patent Application No. 227075/90), pAGE103 [J. Biochem., 101, 1307 (1987)], pAGE210, pAMo, pAMoA and the like.

Any promoter can be used, so long as it can function in an animal cell. Examples include a promoter of IE (immediate early) gene of cytomegalovirus (CMV), SV40 early promoter, a metallothionein promoter, a promoter of retrovirus, a heat shock promoter, SRα promoter and the like. Also, the enhancer of the IE gene of human CMV can be used together with the promoter.

The host cell includes mouse myeloma cell, rat myeloma cell, mouse hybridoma cell, human Namalwa cell, Namalwa KJM-1 cell, human fetal kidney cell, human leukemia cell, African grivet kidney cell, Chinese hamster ovary (CHO) cell, HBT5637 (Japanese Published Unexamined Patent Application No. 299/88) and the like.

The mouse myeloma cell includes SP2/0, NS0 and the like. The rat myeloma cell includes YB2/0 and the like. The human fetal kidney cell includes HEK293 (ATCC: CRL-1573) and the like. The human leukemia cell includes BALL-1 and the like. The African grivet kidney cell includes COS-1, COS-7 and the like.

Introduction of the recombinant DNA into animal cells can be carried out by any of methods for introducing DNA into animal cells, such as electroporation [Cytotechnology, 3, 133 (1990)], the calcium phosphate method (Japanese Published Unexamined Patent Application No. 227075/90), the lipofection method [Proc. Natl. Acad. Sci. USA, 84, 7413 (1987)], and the method described in Virology, 52, 456 (1973).

When an insect cell is used as the host, the protein can be produced by a known method described in, for example, Baculovirus Expression Vectors, A Laboratory Manual, W. H. Freeman and Company, New York (1992), Molecular Biology, A Laboratory Manual, Current Protocols in Molecular Biology, Bio/Technology, 6, 47 (1988) or the like.

Specifically, a recombinant gene transfer vector and baculovirus are co-transfected into an insect cell to obtain a recombinant virus in a supernatant of the culture of its insect cell, and then an insect cell is infected with the resulting recombinant virus to produce the protein.

The transfer vector used in the method includes pVL1392, pVL1393 and pBlueBacIII (all manufactured by Invitrogen), and the like.

The baculovirus includes Autographa californica nuclear polyhedrosis virus which infects insects of the family Barathra and the like.

The insect cell includes Spodoptera frugiperda ovary cell, Trichoplusia ni ovary cell, silkworm ovary-derived culturing cell and the like.

Spodoptera frugiperda ovary cell includes Sf9 and Sf21 (Baculovirus Expression Vectors, A Laboratory Manual) and the like. Trichoplusia ni ovary cell includes High 5 and BTI-TN-5B1-4 (manufactured by Invitrogen) and the like. The cell line derived from silkworm ovary cell includes Bombyx mori N4 and the like.

The method for co-transfecting the above transfer vector and the above baculovirus for the preparation of the recombinant virus includes the calcium phosphate method (Japanese Published Unexamined Patent Application No. 227075/90), the lipofection method [Proc. Natl. Acad. Sci. USA, 84, 7413 (1987)] and the like.

When a plant cell is used as the host cell, the expression vector includes Ti plasmid, a tobacco mosaic virus vector, and the like.

As the promoter, any promoter can be used, so long as it can function in a plant cell. Examples include 35S promoter of cauliflower mosaic virus (CaMV), rice actin 1 promoter and the like.

The host cell includes a plant cell and the like, such as tobacco, potato, tomato, carrot, soybean, rape, alfalfa, rice, wheat and barley.

Introduction of the recombinant vector is carried out by the method for introducing DNA into a plant cell, such as Agrobacterium method (Japanese Published Unexamined Patent Application No. 140885/84, Japanese Published Unexamined Patent Application No. 70080/85, WO 94/00977), electroporation (Japanese Published Unexamined Patent Application No. 251887/85) and the method using a particle gun (Japanese Patent Nos. 2606856 and 2517813).

The protein having β1,3-N-acetylglucosaminyltransferase activity can be produced by culturing the transformant thus obtained in a medium to produce and accumulate the protein having β1,3-N-acetylglucosaminyltransferase activity in the culture, and recovering it from the culture.

Culturing of the transformant used in the process for production of the present invention in a medium is carried out according to the conventional method as used in culturing of the host.

As a medium for culturing the transformant obtained by using, as the host, prokaryote such as Escherichia coli, or eukaryote such as yeast, either a natural medium or a synthetic medium may be used, so long as it contains a carbon source, a nitrogen source, an inorganic salt and the like which can be assimilated by the organism and the transformant can be cultured efficiently.

Any carbon source can be used, so long as the organism can assimilate, and it includes carbohydrates, such as glucose, fructose, sucrose, molasses containing them, starch and starch hydrolysate; organic acids, such as acetic acid and propionic acid; alcohols, such as ethanol and propanol; and the like.

The nitrogen source includes ammonia, various ammonium salts of inorganic acids or organic acids, such as ammonium chloride, ammonium sulfate, ammonium acetate and ammonium phosphate; other nitrogen-containing compounds; peptone; meat extract; yeast extract; corn steep liquor; casein hydrolysate; soybean meal and soybean meal hydrolysate; various fermented cells and digested matter thereof; and the like.

The inorganic salt includes potassium dihydrogen phosphate, dipotassium hydrogen phosphate, magnesium phosphate, magnesium sulfate, sodium chloride, ferrous sulfate, manganese sulfate, copper sulfate, calcium carbonate and the like.

Culturing is usually carried out under aerobic conditions by shaking culture, submerged spinner culture under aeration or the like. The culturing temperature is preferably from 15 to 40° C., and the culturing time is generally from 5 hours to 7 days. The pH of the medium is preferably maintained at 3.0 to 9.0 during the culturing. The pH can be adjusted using inorganic or organic acid, an alkali solution, urea, calcium carbonate, ammonia or the like.

Also, antibiotics, such as ampicillin and tetracycline, can be added to the medium during culturing, if necessary.

When a microorganism transformed with an expression vector containing an inducible promoter is cultured, an inducer can be added to the medium, if necessary. For example, isopropyl-β-D-thiogalactopyranoside or the like can be added to the medium when a microorganism transformed with an expression vector containing lac promoter is cultured; or indoleacrylic acid or the like can be added thereto when a microorganism transformed with an expression vector containing trp promoter is cultured.

The medium for culturing a transformant obtained using an animal cell as the host includes generally used RPMI 1640 medium [*The Journal of the American Medical Association*, 199, 519 (1967)], Eagle's MEM medium [*Science*, 122, 501 (1952)], DMEM medium [*Virology*, 8, 396 (1959)], and 199 Medium [*Proceeding of the Society for the Biological Medicine*, 73, 1 (1950)], as well as media of which fetal calf serum or the like has been added to the above media and the like.

Culturing is generally carried out at pH 6 to 8 and at 25 to 40° C. for 1 to 7 days in the presence of 5% $CO_2$ or the like.

Furthermore, if necessary, antibiotics such as kanamycin, penicillin and streptomycin, can be added to the medium during the culturing.

The medium for culturing a transformant obtained using an insect cell as the host includes generally used TNM-FH medium (manufactured by Pharmingen), Sf-900 II SFM (manufactured by Life Technologies), ExCell 400 and ExCell 405 (both manufactured by JRH Biosciences), Grace's Insect Medium [*Nature*, 195, 788 (1962)] and the like.

Culturing is generally carried out at pH 6 to 7 and at 25 to 30° C. for 1 to 5 days or the like.

Furthermore, if necessary, antibiotics such as gentamicin can be added to the medium during the culturing.

A transformant obtained by using a plant cell as the host cell can be used as the cell or after differentiating to a plant cell or organ. The medium used in the culturing of the transformant includes Murashige and Skoog (MS) medium, White medium, media to which a plant hormone, such as auxin or cytokinine, has been added, and the like.

Culturing is carried out generally at a pH 5 to 9 and at 20 to 40° C. for 3 to 60 days.

Also, antibiotics, such as kanamycin and hygromycin, can be added to the medium during the culturing, if necessary.

As described above, the protein having β1,3-N-acetylglucosaminyltransferase activity can be produced by culturing a transformant derived from a microorganism, animal cell, insect cell or plant cell containing the recombinant DNA which comprises the DNA encoding the protein according to the general culturing method to produce and accumulate the protein, and recovering the protein from the culture.

In the production of the protein having β1,3-N-acetylglucosaminyltransferase activity, the protein can be produced so as to have a structure as it is or can be produced as a secretory protein having a signal sequence or a fusion protein according to the method described in *Molecular Cloning*, Second Edition and the like.

The protein to be fused includes β-galactosidase, protein A, IgG binding region of protein A, chloramphenicol acetylransferase, poly(Arg), poly(Glu), protein G, maltose binding protein, glutathione S-transferase, polyhistidine chain (Histag), S peptide, DNA binding protein domain, Tac antigen, thioredoxin, green fluorescent protein, FLAG peptide, epitope of any antibody, and the like [Akio Yamakawa, *Experimental Medicine (Jikken Igaku)*, 13, 469-474 (1995)].

When the protein having β1,3-N-acetylglucosaminyltransferase activity is produced in a host cell or on an outer membrane of the host cell, the produced protein can be actively secreted extracellularly according to, for example, the method of Paulson et al. [*J. Biol. Chem.*, 264, 17619 (1989)], the method of Lowe et al. [*Proc. Natl. Acad. Sci. USA*, 86, 8227 (1989); *Genes Develop.*, 4, 1288 (1990)], or the methods described in Japanese Published Unexamined Patent Application No. 336963/93, WO94/23021, and the like.

Specifically, the protein of the present invention can be actively secreted extracellularly by producing it in the form that a signal peptide has been added to the side of N-terminal of a protein containing an active site of the protein having β1,3-N-acetylglucosaminyltransferase activity according to the recombinant DNA technique.

Furthermore, the protein production can be increased utilizing a gene amplification system using a dihydrofolate reductase gene or the like according to the method described in Japanese Published Unexamined Patent Application No. 227075/90.

Moreover, the protein having β1,3-N-acetylglucosaminyltransferase activity can be produced by rediferentiating a gene-introduced animal or plant cell to develop a gene-introduced transgenic animal individual (transgenic nonhuman animal) or plant individual (transgenic plant), and using the individual.

When the transformant is the animal individual or plant individual, the protein can be produced by breeding or cultivating it to produce and accumulate the protein, and recovering the protein from the animal individual or plant individual.

The process for producing the protein having β1,3-N-acetylglucosaminyltransferase activity using the animal individual includes a method for producing the protein of the present invention in a nonhuman animal developed by introducing a gene according to a known method [*Am. J. Clin. Nutr.*, 63, 639S (1996), *Am. J. Clin. Nutr*, 63, 627S (1996), *Bio/Technology*, 9, 830 (1991)].

In the animal individual, the protein can be produced by breeding a transgenic nonhuman animal to which the DNA encoding the protein having β1,3-N-acetylglucosaminyltransferase has been introduced to produce and accumulate the protein in the animal, and recovering the protein from the animal. The protein produced in the animal is accumulated in milk (Japanese Published Unexamined Patent Application No. 309192/88), egg, and the like. Any promoter can be used, so long as it can function in the animal. Suitable examples include an α-casein promoter, a β-casein promoter, a β-lactoglobulin promoter, a whey acidic protein promoter, and the like, which are specific for mammary glandular cells.

The process for producing the protein having β1,3-N-acetylglucosaminyltransferase activity using the plant individual includes a process for producing the protein by cultivating a transgenic plant to which the DNA encoding the protein of the present invention is introduced by a known method [*Tissue Culture (Soshiki Baiyo)*, 20 (1994), *Tissue Culture (Soshiki Baiyo)*, 21 (1995), *Trends Biotechnol.*, 15, 45 (1997)] to produce and accumulate the protein in the plant, and recovering the protein from the plant.

The protein produced by the process for production of the protein of the present invention can be isolated and purified by using the general method for isolating and purifying an enzyme.

For example, when the protein having β1,3-N-acetylglucosaminyltransferase activity is produced as a soluble product in the host cells, the cells are collected by centrifugation after culturing, suspended in an aqueous buffer, and disrupted using an ultrasonicator, a French press, a Manton Gaulin homogenizer, a Dynomill, or the like to obtain a cell-free extract.

From the supernatant obtained by centrifuging the cell-free extract, a purified product can be obtained by the general method used for isolating and purifying an enzyme, for example, solvent extraction, salting-out using ammonium sulfate or the like, desalting, precipitation using an organic solvent, anion exchange chromatography using a resin such as diethylaminoethyl (DEAE)-Sepharose or DIAION HPA-75 (manufactured by Mitsubishi Chemical), cation exchange chromatography using a resin such as S-Sepharose FF (manufactured by Pharmacia), hydrophobic chromatography using a resin such as butyl sepharose or phenyl sepharose, gel filtration using a molecular sieve, affinity chromatography, chromatofocusing, or electrophoresis such as isoelectronic focusing, alone or in combination thereof.

When the protein is produced as an inclusion body in the host cells, the cells are collected in the same manner, disrupted and centrifuged to recover the protein as the precipitate fraction, and then the inclusion body of the protein is solubilized with a protein-denaturing agent.

The solubilized solution is diluted or dialyzed in a solution free from a protein denaturing agent or a solution having a diluted concentration of a protein denaturing agent in such a degree that the protein is not denatured to thereby constitute the normal tertiary structure of the protein, and then a purified product of the protein can be obtained by a purification/isolation method similar to the above.

When the protein having β1,3-N-acetylglucosaminyltransferase activity or derivatives such as its glycosylated-derivatives are secreted out of cells, the protein or its derivatives such as the glycosylated-derivatives can be collected in the culture supernatant.

Specifically, the culture medium is treated in a manner similar to the above, such as centrifugation to obtain a solubilized fraction, from which a purified product can be obtained using a purification/isolation method similar to the above.

The protein obtained by the above method includes a protein comprising the amino acid sequence represented by SEQ ID NO:1.

Furthermore, the protein having β1,3-N-acetylglucosaminyltransferase activity is produced as a fusion protein with other protein, and can be purified using affinity chromatography using a substance having affinity to the fusion protein. For example, the fusion protein having β1,3-N-acetylglucosaminyltransferase activity is produced as a fusion protein with protein A according to the method of Lowe et al. [*Proc. Natl. Acad. Sci. USA*, 86, 8227 (1989); *Genes Develop.*, 4, 1288 (1990)], or the method described in Japanese Published Unexamined Patent Application No. 336963/93 or WO94/23021, and the fusion protein can be purified by affinity chromatography using immunoglubulin G.

Moreover, the protein having β1,3-N-acetylglucosaminyltransferase activity is produced as a fusion protein with Flag peptide, and the fusion protein can be purified by affinity chromatography using an anti-Flag antibody [*Proc. Natl. Acad. Sci., USA*, 86, 8227 (1989), *Genes Develop.*, 4, 1288 (1990)]. In addition, purification can be carried out by affinity chromatography using the antibody against the polypeptide per se.

Based on the amino acid sequence information of the protein thus obtained, the protein having β1,3-N-acetylglucosaminyltransferase can be produced by a chemical synthesis method, such as Fmoc (fluorenylmethyloxycarbonyl) method or tBoc (t-butyloxycarbonyl) method. It can also be chemically synthesized using a peptide synthesizer manufactured by Advanced ChemTech, Perkin-Elmer, Pharmacia, Protein Technology Instrument, Synthecell-Vega, PerSeptive, Shimadzu Corporation, or the like.

(3) Preparation of N-acetylglucosamine-containing Complex Carbohydrate

An N-acetylglucosamine-containing complex carbohydrate can be produced in an aqueous medium by allowing a culture of the transformant obtained by the culturing described in the above item [2] or a treated product of the culture as an enzyme source, uridine 5'-diphosphate N-acetylglucosamine and an acceptor complex carbohydrate to be present in the aqueous medium to produce and accumulate the N-acetylglucosamine-containing complex carbohydrate in the aqueous medium.

The treated product of the culture includes a concentrated product of the culture, a dried product of the culture, cells obtained by centrifuging the culture, a dried product of the cells, a freeze-dried product of the cells, a surfactant-treated product of the cells, an ultrasonic-treated product of the cells, a mechanically disrupted product of the cells, a solvent-treated product of the cells, an enzyme-treated product of the cells, a protein fraction of the cells, an immobilized product of the cells, an enzyme preparation obtained by extracting from the cell, and the like.

The acceptor complex carbohydrate includes a complex carbohydrate comprising an oligosaccharide having galactose in its non-reducing terminal, preferably a complex carbohydrate comprising an oligosaccharide having a structure selected from the group consisting of lactose, N-acetyllactosamine, lacto-N-tetraose and lacto-N-neotetraose in the non-reducing terminal, and more preferably a complex carbohydrate selected from the group consisting of lactose, N-acetyllactosamine, lacto-N-tetraose and lacto-N-neotetraose.

The enzyme source used in the production of the N-acetylglucosamine-containing complex carbohydrate is used in a concentration of 1 mU/l to 1,000 U/l, preferably 10 mU/l to 500 U/l, when the activity capable of forming 1 μmol of N-acetylglucosamine-containing complex carbohydrate at 37° C. in 1 minute is defined as 1 unit (U).

The aqueous medium used in the production of the N-acetylglucosamine-containing complex carbohydrate includes water; a buffer such as a phosphate buffer, a carbonate buffer, an acetate buffer, a borate buffer, a citrate buffer and a tris buffer; alcohol, such as methanol and ethanol; ester such as ethyl acetate; ketone such as acetone; amide such as acetamide; and the like. Also, the culture broth of the microorganisms used as the enzyme source can be used as an aqueous medium.

In the production of the N-acetylglucosamine-containing complex carbohydrate, a surfactant or an organic solvent may be added, if necessary. Any surfactant capable of accelerating the formation of an N-acetylglucosamine-containing complex carbohydrate can be used as the surfactant. Examples include nonionic surfactants such as polyoxyethylene octadecylamine (e.g., Nymeen S-215, manufactured by Nippon Oil & Fats); cationic surfactants, such as cetyltrimethylammonium bromide and alkyldimethyl benzylammoniumchloride (e.g., Cation F2-40E, manufactured by Nippon Oil & Fats); anionic surfactants such as lauroyl sarcosinate; tertiary amines such as alkyldimethylamine (e.g., Tertiary Amine FB, manufactured by Nippon Oil & Fats); and the like, which are used alone or as a mixture of two or more. The surfactant is used generally in a concentration of 0.1 to 50 g/l. The organic solvent includes xylene, toluene, fatty acid alcohol, acetone, ethyl acetate, and the like, which are used in a concentration of generally 0.1 to 50 ml/l.

The production reaction for the N-acetylglucosamine-containing complex carbohydrate is carried out in an aqueous medium having a pH 5 to 10, preferably pH 6 to 8, at 20 to 50° C. for 1 to 96 hours. In the production reaction, inorganic salts, such as $MnCl_2$ and $MgCl_2$, can be added, if necessary.

The amount of the N-acetylglucosamine-containing complex carbohydrate produced in the aqueous medium can be determined, for example, using a carbohydrate analysis system manufactured by Dionex [*Anal. Biochem.*, 189: 151 (1990)] or the like.

The N-acetylglucosamine-containing complex carbohydrate produced in the aqueous medium can be recovered by the ordinary method using activated carbon, an ion exchange resin or the like.

BEST MODE FOR CARRYING OUT THE INVENTION

Example 1

Construction of a Strain Expressing a β1,3-N-acetylglucosaminyltransferase Gene Derived from *Pasteurella multocida*

*Pasteurella multocida* PM70 was cultured by a known method [*FEMS Microbiol. Lett.*, 166, 289 (1998)].

After the culturing, chromosomal DNA of the microorganism was isolated and purified by the method described in *Current Protocols in Molecular Biology*.

Using DNA fragments having the nucleotide sequences represented by SEQ ID NOs:3 and 4, which had been synthesized using a DNA synthesizer Model 8905 manufactured by Perceptive Biosystems, a DNA fragment containing pm0511 considered to be a glycosyltransferase gene in the total nucleotide sequence of the genomic DNA in *Pasteurella multocida* PM70 was amplified by the following method.

PCR was carried out using the above synthetic DNA fragments as a primer set and using chromosomal DNA of *Pasteurella multocida* PM70 as the template. The PCR was carried out using 40 µl of a reaction solution containing 0.1 µg of the chromosomal DNA, 0.5 µmol/l of each of the primers, 2.5 units of Pfu DNA polymerase (manufactured by Stratagene), 4 µl of 10× buffer for Pfu DNA polymerase and 200 µmol/l of each deoxyNTP, and by repeating 30 times of a step consisting of 1 minute at 94° C., 2 minutes at 42° C. and 3 minutes at 72° C.

A 1/10 volume of the reaction solution was subjected to agarose gel electrophoresis to confirm that the fragment of interest was amplified, and then the remaining reaction solution was mixed with the same volume of TE [10 mmol/l Tris-HCl and 1 mmol/l EDTA (pH 8.0)] saturated phenol/chloroform (1 vol/1 vol).

After centrifugation of the mixed solution, the thus obtained upper layer was mixed with 2 volumes of cold ethanol and allowed to stand at −80° C. for 30 minutes. A precipitate of DNA was obtained by centrifuging the solution, and the DNA precipitate was dissolved in 20 µl of TE.

Using 5 µl of the dissolved solution, the DNA was digested with restriction enzymes HindIII and BamHI, the resulting DNA fragments were separated by agarose gel electrophoresis, and then a DNA fragment of 0.9 kb was recovered using Gene Clean II Kit (purchased from Funakoshi).

After 0.2 µg of pBluescript II SK(+) was digested with restriction enzymes HindIII and BamHI, the resulting DNA fragments were separated by agarose gel electrophoresis, and then a DNA fragment of 2.9 kb was recovered in the same manner.

The 0.9 kb and 2.9 kb fragments were ligated at 16° C. for 16 hours using a ligation kit. *Escherichia coli* NM522 was transformed using the ligation reaction solution in accordance with the above known method, and the transformant was spread on an LB agar medium [10 g/l Bacto-Tryptone (manufactured by Difco), 10 g/l yeast extract (manufactured by Difco), 5 g/l sodium chloride and 15 µl agarose] containing 50 µg/ml ampicillin and then cultured overnight at 30° C.

A plasmid was extracted from the thus formed transformant colonies in accordance with the above known method, structure of the plasmid was confirmed by restriction enzyme digestion, and the plasmid was named pPM0511SK. The plasmid pPM0511SK has been deposited on Oct. 18, 2001, as FERM BP-7778 in International Patent Organism Depositary, National Institute of Advanced Industrial Science and Technology (Central 6, 1-1, Higashi 1-Chome Tsukuba, Ibaraki, 305-8566, Japan).

Next, 0.2 µg of pPM0511SK was digested with restriction enzymes HindIII and BamHI, the resulting DNA fragments were separated by agarose gel electrophoresis, and then a DNA fragment of 0.9 kb was recovered. After 0.2 µg of pTrS31 DNA was digested with restriction enzymes HindIII and BamHI, the resulting DNA fragments were separated by agarose gel electrophoresis, and then a DNA fragment of 4.3 kb was recovered in the same manner.

The 0.9 kb and 4.3 kb DNA fragments were ligated at 16° C. for 16 hours using the ligation kit.

*Escherichia coli* NM522 was transformed by using the ligation reaction solution in accordance with the above known method, and the transformant was spread on the LB agar medium containing 50 µg/ml of ampicillin and then cultured overnight at 30° C.

Figure 1:
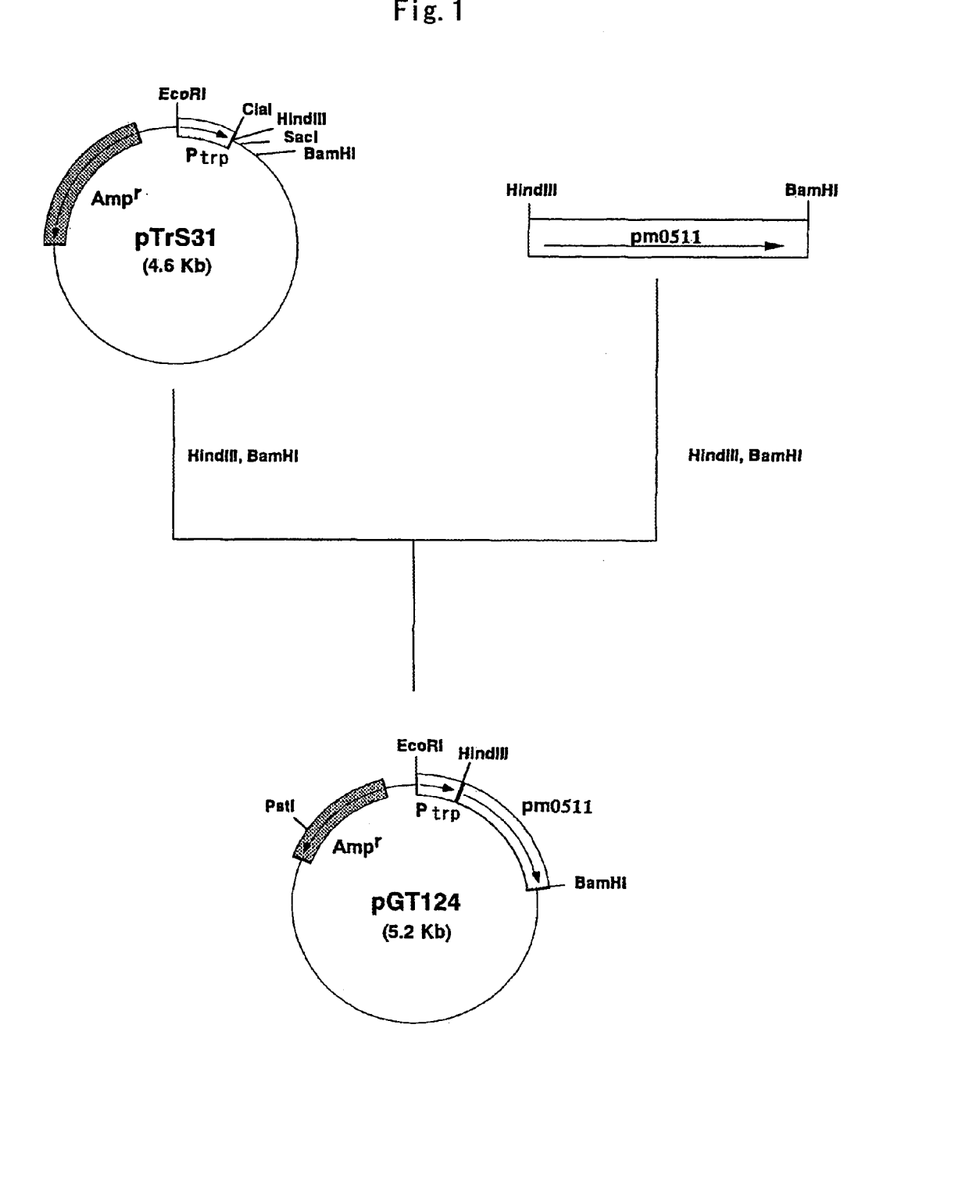
FIG. 1 shows construction steps of β1,3-N-acetylglucosaminyltransferase gene expression plsmid pGT124. In the drawing, $Amp^r$ represents an ampicillin-resistant gene; $P_{trp}$ represents tryptophane promoter; and pm0511 represents a gene encoding an β1,3-N-acetylglucosaminyltransferase.

A plasmid was extracted from the thus formed transformant colonies in accordance with the above known method to thereby obtain an expression plasmid pGT124. Structure of the plasmid was confirmed by restriction enzyme digestion (FIG. 1).

Example 2

Production of GlcNAcβ1,3Galβ1,4Glc

*Escherichia coli* NM522/pGT124 obtained in Example 1 was inoculated into a thick test tube charged with 8 ml of LB medium containing 50 μg/ml ampicillin and cultured at 28° C. for 17 hours. The culture was inoculated into a thick test tube charged with 8 ml of LB medium containing 50 μg/ml ampicillin, with an inoculum size of 1%, followed by culturing at 37° C. for 7 hours. Wet cells were obtained by centrifuging 0.1 ml of the culture. Since the wet cells could be stored at −20° C., if necessary, it was able to use them by thawing prior to use.

The reaction was carried out at 37° C. for 10 hours in 0.1 ml of a reaction solution comprising the NM522/pGT124 wet cells obtained in the above, 50 mmol/l of a citrate buffer (pH 7.0), 10 mmol/l $MnCl_2$, 10 mmol/l lactose, 10 mmol/l UDP-N-acetylglucosamine and 4 g/l Nymeen S-215.

After completion of the reaction, the reaction product was analyzed by using a sugar analyzer manufactured by Dionex (DX-500) under the following analyzing conditions to confirm that 75 mg/l of GlcNAcβ1,3Galβ1,4Glc was formed and accumulated in the reaction solution.

Analyzing Conditions:
  Column: CarboPAC PA10
  Eluent: eluent A; $H_2O$, eluent B; 500 mmol/l NaOH
  Gradient: Linear gradient from a composition of 8% eluent B at 0 minute to a composition of 20% eluent B spending 21 minutes.
  Detector: Pulsed amperometry detector

INDUSTRIAL APPLICABILITY

According to the present invention, a β1,3-N-acetylglucosaminyltransferase can be produced in a large amount. Also, an N-acetylglucosamine-containing complex carbohydrate can be produced efficiently by using the enzyme.

Free Text of Sequence Listing:
SEQ ID NO:3—Description of artificial sequence: Synthetic DNA
SEQ ID NO:4—Description of artificial sequence: Synthetic DNA

---

The invention claimed is:

1. A process for producing an N-acetylglucosamine-containing complex carbohydrate, which comprises:

allowing (a) a culture of a transformant capable of producing a protein selected from the group consisting of (i) a protein comprising the amino acid sequence of SEQ ID NO:1 and (ii) a protein which has a homology of at least 95% with the amino acid sequence of SEQ ID NO:1, and which has β1,3-N-acetylglucosaminyltransferase activity, or a treated culture of the transformant as an enzyme source, (b) uridine 5'-diphosphate N-acetylglucosamine and (c) an acceptor complex carbohydrate comprising an oligosaccharide having galactose in its non-reducing terminal to be present in an aqueous medium, producing and accumulating the N-acetylglucosamine-containing complex carbohydrate in the aqueous medium, and recovering the N-acetylglucosamine-containing complex carbohydrate from the aqueous medium, wherein the treated culture is selected from the group consisting of a concentrated culture, a dried culture, cells obtained by centrifuging the culture, dried cells and freeze-dried cells which comprise whole cells and has the enzymatic activity of the culture.

2. The process according to claim 1, wherein the oligosaccharide having galactose in the non-reducing terminal is selected from the group consisting of lactose, N-acetyllactosamine, lacto-N-tetraose and lacto-N-neotetraose.

3. The process according to claim 1, wherein the acceptor complex carbohydrate is selected from the group consisting of lactose, N-acetyllactosamine, lacto-N-tetraose, and lacto-N-neotetraose.

4. A process for producing an N-acetylglucosamine-containing complex carbohydrate, which comprises:

allowing (a) a culture of a transformant which comprises a recombinant DNA comprising a DNA selected from the group consisting of (i) a DNA comprising the nucleotide sequence of SEQ ID NO:2 and (ii) a DNA which hybridizes with a DNA comprising the nucleotide sequence of SEQ ID NO:2 at 65° C. in the presence of 0.7-1.0 mol/l NaCl using a filter on which a DNA prepared from colonies or plaques is immobilized, and then washing the filter with 0.1× to 2×SSC solution at 65° C., and which encodes a protein having β1,3-N-acetylglucosaminyltransferase activity, or a treated culture as an enzyme source, (b) uridine 5'-diphophate N-acetylglucosamine and (c) an acceptor complex carbohydrate comprising an oligosaccharide having galactose in its non-reducing terminal to be present in an aqueous medium, producing and accumulating the N-acetylglucosamine-containing complex carbohydrate in the aqueous medium, and recovering the N-acetylglucosamine-containing complex carbohydrate from the aqueous medium, wherein the treated culture is selected from the group consisting of a concentrated culture, a dried culture, cells obtained by centrifuging the culture, dried cells and freeze-dried cells which comprise whole cells and has the enzymatic activity of the culture.

5. The process according to claim 4, wherein the transformant uses a microorganism as a host cell.

6. The process according to claim 5, wherein the microorganism is *Escherichia coli*.

7. The process according to claim 4, wherein the oligosaccharide having galactose in the non-reducing terminal is selected from the group consisting of lactose, N-acetyllactosamine, lacto-N-tetraose and lacto-N-neotetraose.

8. The process according to claim 4, wherein the acceptor complex carbohydrate is selected from the group consisting of lactose, N-acetyllactosamine, lacto-N-tetraose and lacto-N-neotetraose.

* * * * *

UNITED STATES PATENT AND TRADEMARK OFFICE
CERTIFICATE OF CORRECTION

PATENT NO. : 7,309,587 B2
APPLICATION NO. : 10/493493
DATED : December 18, 2007
INVENTOR(S) : Tetsuo Endo et al.

It is certified that error appears in the above-identified patent and that said Letters Patent is hereby corrected as shown below:

ON THE TITLE PAGE ITEM [73]:
Assignee, "Kyowa Jakko Kogyo Co., Ltd., Tokyo (JP)" should read
--Kyowa Hakko Kogyo Co., Ltd., Tokyo (JP)--.

COLUMN 5:
Line 32, "includes" should read --includes:--.

COLUMN 8:
Line 34, "lie" should read --lay--.

COLUMN 15:
Line 39, "plsmid" should read --plasmid--; and
Line 42, "an" should read --a--.

Column 23:
Line 2, "5'-diphophate" should read --5'-diphosphate--.

Signed and Sealed this

Twenty-fourth Day of June, 2008

JON W. DUDAS
*Director of the United States Patent and Trademark Office*